(12) United States Patent
Bennish, Jr. et al.

(10) Patent No.: US 6,503,183 B1
(45) Date of Patent: Jan. 7, 2003

(54) REINFORCED STERILIZABLE CONTAINERS

(75) Inventors: Gerald Edward Bennish, Jr., Antioch, IL (US); Robert William Hinley, Jr., Spring Grove, IL (US)

(73) Assignee: Rexam Medical Packaging, Inc., Charlotte, NC (US)

( * ) Notice: Subject to any disclaimer, the term of this patent is extended or adjusted under 35 U.S.C. 154(b) by 0 days.

(21) Appl. No.: 09/534,518

(22) Filed: Mar. 24, 2000

Related U.S. Application Data

(62) Division of application No. 09/212,095, filed on Dec. 15, 1998, now Pat. No. 6,098,800.
(60) Provisional application No. 60/068,234, filed on Dec. 19, 1997.

(51) Int. Cl.[7] ................................................ B05C 1/100
(52) U.S. Cl. ........................................ 493/334; 493/382
(58) Field of Search ................................. 493/331, 334, 493/374, 379, 382; 383/200, 205; 206/439

(56) References Cited

U.S. PATENT DOCUMENTS

| | | | |
|---|---|---|---|
| 2,991,000 A | 7/1961 | Spees | |
| 3,460,742 A | 8/1969 | Langdon | |
| 3,595,465 A | 7/1971 | Vaillancourt | |
| 3,754,700 A | 8/1973 | Bonk | |
| 3,768,725 A | 10/1973 | Pilaro | |
| 3,938,658 A | 2/1976 | Rohde | |
| 3,991,881 A | 11/1976 | Augurt | |
| 4,057,144 A | 11/1977 | Schuster | |
| 4,097,236 A | 6/1978 | Daly et al. | |
| 4,306,656 A | * 12/1981 | Dahlem | |
| 4,352,429 A | * 10/1982 | Newman | |
| 4,367,816 A | 1/1983 | Wilkes | |
| 4,482,053 A | 11/1984 | Alpern et al. | |
| 4,510,621 A | 4/1985 | Sak et al. | |
| 4,550,831 A | 11/1985 | Whitford | |
| 4,660,721 A | * 4/1987 | Mykleby | |
| 4,948,028 A | 8/1990 | Vollowitz | |
| 5,064,664 A | 11/1991 | Hustad | |
| 5,178,277 A | 1/1993 | Brown et al. | |
| 5,439,102 A | 8/1995 | Brown et al. | |
| 5,459,978 A | 10/1995 | Weiss et al. | |
| 5,551,781 A | 9/1996 | Wilkes et al. | |
| 5,816,403 A | 10/1998 | Wilkes et al. | |
| 6,098,800 A | * 8/2000 | Bennish, Jr. et al. | |
| 6,251,489 B1 | * 6/2001 | Weiss et al. | |

* cited by examiner

Primary Examiner—Eugene Kim
(74) Attorney, Agent, or Firm—Alston & Bird LLP

(57) ABSTRACT

A reinforced container having a header or tear strip, the header comprising an affixed tape having an adhesive and a polymeric backing, the backing positioned to face the container, such that upon heat sealing, the polymeric film-to-header weld seal is stronger than the header-to-container seal ordinarily achieved.

3 Claims, 4 Drawing Sheets

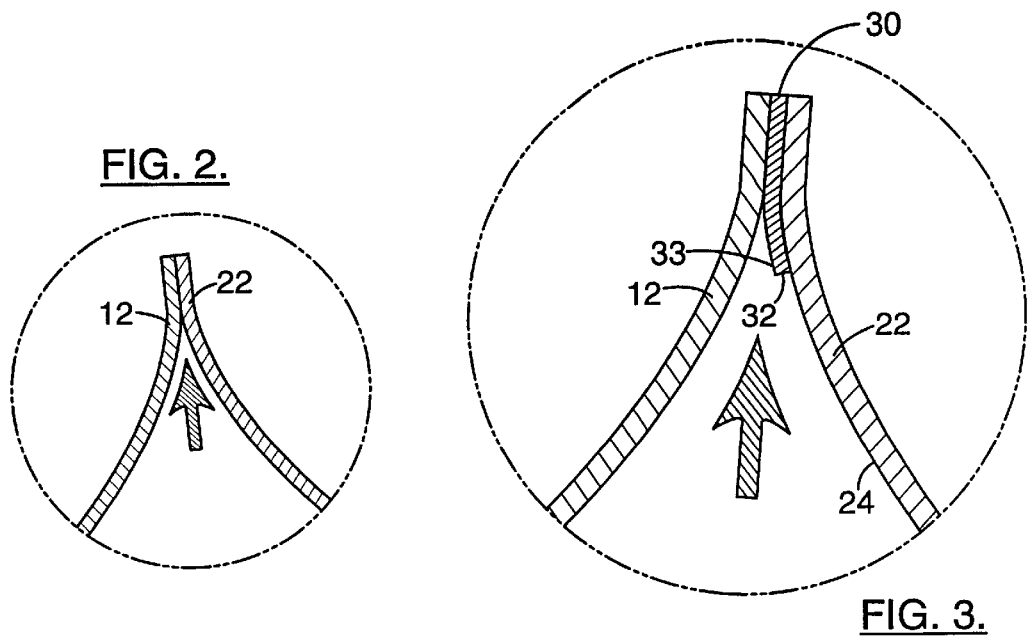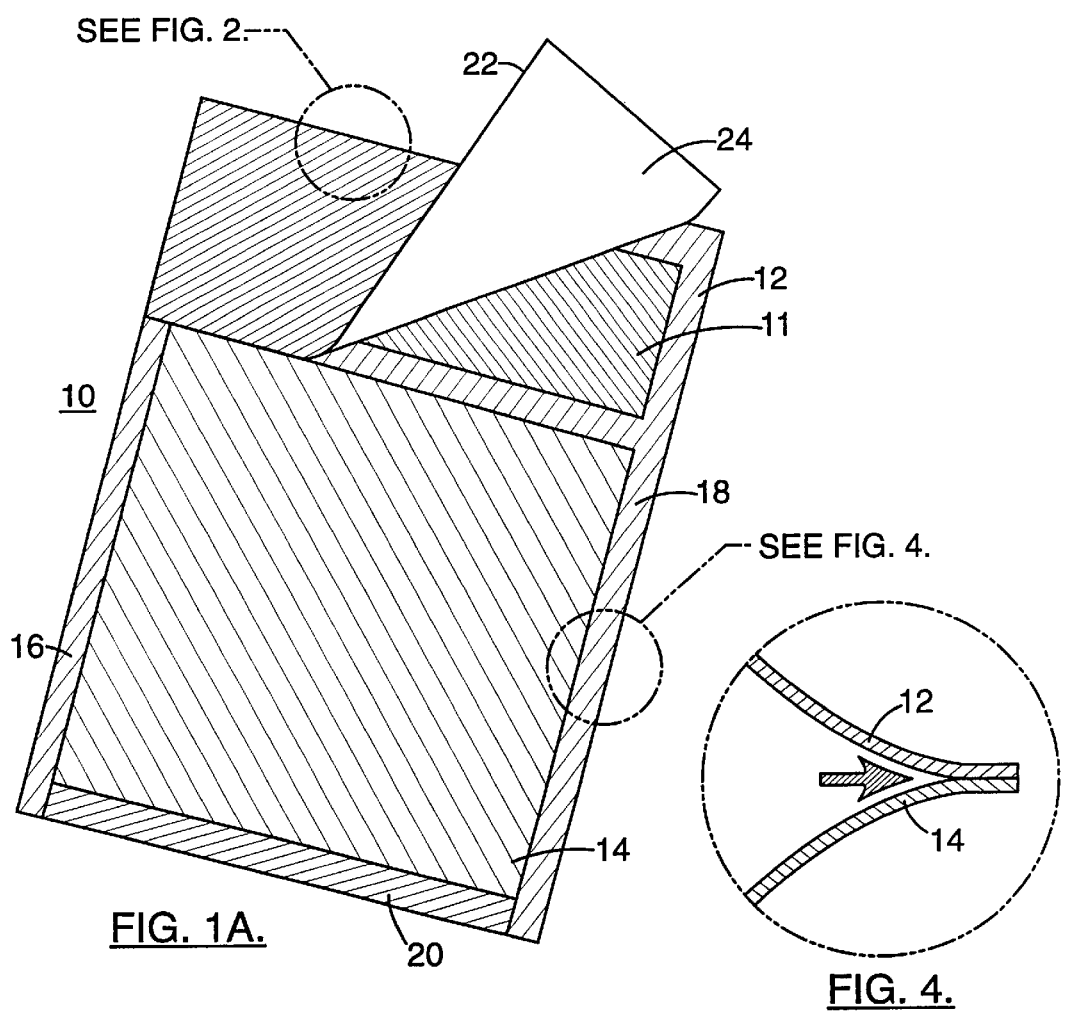

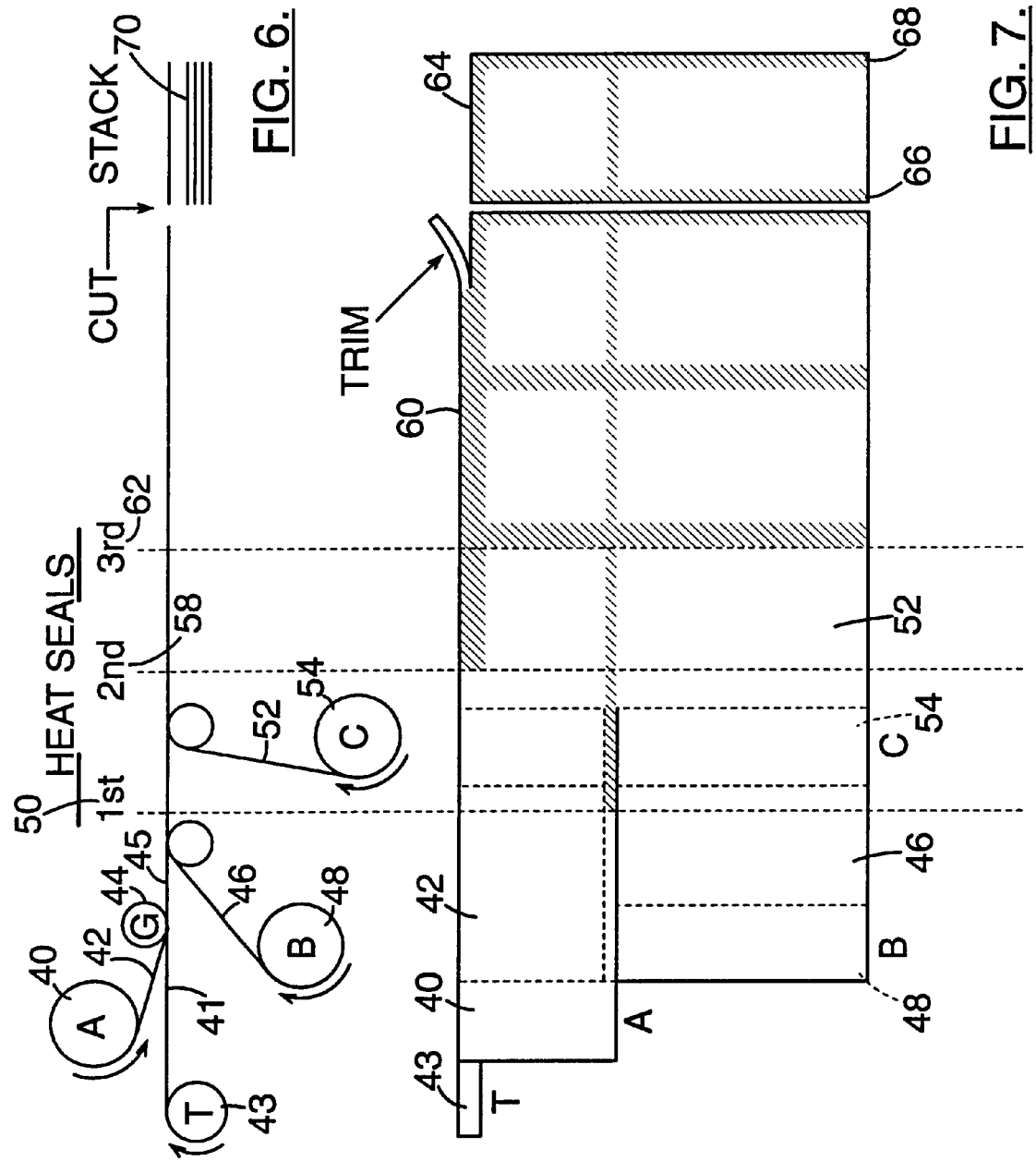

REINFORCED STERILIZABLE CONTAINERS

This application is a Divisional Application of U.S. patent application Ser. No.: 09/212,095 now U.S. Pat. No. 6,098,800, filed Dec. 15, 1998, and claims the benefit of U.S. Provisional Application No. 60/068,234, filed Dec. 19, 1997.

FIELD OF THE INVENTION

The present invention relates to packages and containers, preferably sterilizable containers used to house medical devices in a sterile environment. More specifically, the present invention relates to heat sealable, sterilizable polymeric bags including those having at least a portion of the bags comprising headers preferably made from a porous material to facilitate passage of a sterilizing agent. The present invention also relates to sterilizable plastic bags having headers made from polymeric film with such bags capable of being subjected to radiation sterilization.

BACKGROUND OF THE INVENTION

Sterilizable containers in the form of pouches or bags are popular vehicles for storing and transporting sterile medical devices, including instruments, dressings, drapes, etc. Such pouches often utilize heat-sealed transparent plastic sheets, for example low density polyethylene, positioned face-to-face and sealed around the common periphery. Such packages often feature an access opening through which the contents of the package are removed, once the package is opened. Access openings are covered with a sealable strip commonly referred to as a "header". The header may be made from a porous or non-porous material and is sealed to one or both of the plastic sheets to cover the access opening. The header is often made from a porous membrane and not only functions as a cover for the access opening, but also facilitates sterilizing the package contents. The porous characteristics of the membrane allow a sterilizing medium, such as sterilizing gas (e.g. ethylene oxide, etc.) or steam, to pass into and out of the pouch, while forming a sterile barrier against bacteria or other contaminants. The header also may be made from a nonporous material such as a polymeric film. Radiation sterilization may be used when the header is made from a nonporous material. Further, headers often serve as tear strips (or peelable strips commonly referred to as "tear strips" herein) and allow a package user to remove the strip to gain access to the package through the access opening. When porous headers are desired, such porous membranes are most often made from a breathable medical grade paper or non-woven fabric, for example, medical grade Tyvek® (DuPont Company).

The way in which a header is sealed to a sterilizable package is often critical to the package's success in the marketplace. For example, if the header is sealed too tightly to the package, header removal by peeling will be made more difficult or impossible. However, to properly sterilize the package, the header must be adhered securely to the package. The repeated sterilizing protocols required for the sterilizing medium to enter and leave the package under repeated vacuum and pressure, will cause the header to separate from the package if the header is not adhered securely enough. Therefore, much research has gone into arriving at the proper combination of header-to-bag seal strength versus header peelability.

Aseptic presentation is the introduction of the contents of a sterilized package into a sterile field without compromising the sterility of the contents of the field. Such presentation is often desirable and packages that permit delivery of contents in this way are also desirable. The release of any particulate matter from the header, upon opening, can compromise the sterile field, and is therefore unacceptable. Regardless of the coating used, it has been a problem for package designers to select the proper coating that both retains the desired porosity of the header to allow sterilizing agent entry at a desired rate, while also providing a good peelable seal between the header and the plastic sheet.

Another problem has been the breaking of the header bag end seal by the package contents as they are loaded into the bag. A package having a suitably strong top seal (at the header) is highly desirable. Additionally, package designers have compromised between peelable seals with a low enough strength to permit easy opening, and high seal strengths on the perimeter of the bag, primarily to end seal, insuring that the contents are retained during sterilization, shipping an handling.

Packages are known having the access opening located at a point away from the upper edge, or top, of the package. In this way, the package contents, upon package inversion, would only come in contact with a heat seal located away from the access opening. See U.S. Pat. No. 5,551,781. In such packages, the tear strip and interlayer between the tear strip and access opening are dimensioned to match the opening made in the upper plastic sheet. The interlayer is applied to the opening, and the porous material tear strip is then placed in contact with the interlayer. This design has many limitations including enhanced processing complexity and cost, as well as a restricted access opening area, as compared with a top opening design.

Other packages are known where the tear strip essentially covers the middle portion of the package which then opens outward. Once again, an interlayer is provided which adds to the overall complexity of the manufacturing process and therefore adds to overall cost. See U.S. Pat. No. 4,367,816.

Therefore, a sterilizable package having an enlarged access opening covered by a porous material that has its edge reinforced to prevent separation by package contents would be highly advantageous to the field of sterilizable packaging. Further, in terms of superior package design, it would be most desirable to have the access opening placed at the top of the package, such that once the header is peeled back or removed, the package could be easily opened and presented aseptically for sterile removal of the package contents.

SUMMARY OF THE INVENTION

According to the present invention, one preferred embodiment relates to a package comprising a first bottom sheet having a first length, and a second top sheet having a second length shorter than the first bottom sheet. The two sheets are placed in registration along their common lower or bottom edge. The two side edges are heat sealed. The bottom edge is left open for contents insertion. The upper edge is comprised only of the longer, lower sheet. The distance from the top edge of the top sheet to the top edge of the bottom sheet represents the dimension of the access opening. This opening is covered by a header made from a porous or nonporous material and acting as a peelable or tear strip which is heat sealed to the top sheet along its top edge and heat sealed to the bottom sheet along its top and side edges.

A tape or film strip having an adhesive on one side and a polymeric (e.g. plastic) backing on its other side is attached to the header along at least one edge, preferably its top edge, although more than one edge may have a tape applied thereto. The adhesive side is placed against the header material and adhered thereto. The header material with adhesive film in place is then placed against the plastic sheets for heat sealing. At the time of heat sealing, the polymeric back of the adhesive film at the top of the header material is heat sealed to the top edge of the lower or bottom polymeric sheet of the package. In this way, a strong polymeric material-to-polymeric material bond, such as a weld seal, is effected along the upper edge of the finished sterilizable container such that upon inversion or loading, any contents, even such contents having significant weight, will not separate the polymeric material-to-polymeric material seal. To further assist in making certain that contents only contact the polymeric material-to-polymeric material seal, an excess of tape preferably is adhered to the header. In this way the contents will not contact the header-to-tape seal. A more complete understanding of the invention can be had by reference to the following detailed description and the attached drawings.

DESCRIPTION OF THE DRAWINGS

FIG. 2 is a close-up cross-sectional view of the package of FIG. 1.

FIG. 3 is a cross-sectional enlarged view of the reinforced heat seal along the top of the package of the present invention.

FIG. 4 is a cross-sectional view of the bag side seal (non-peelable) of the package of FIG. 1.

FIG. 6 shows a schematic view of the manufacturing process of the present invention.

FIG. 7 is an overhead plan schematic view of the manufacturing process of the present inventions.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
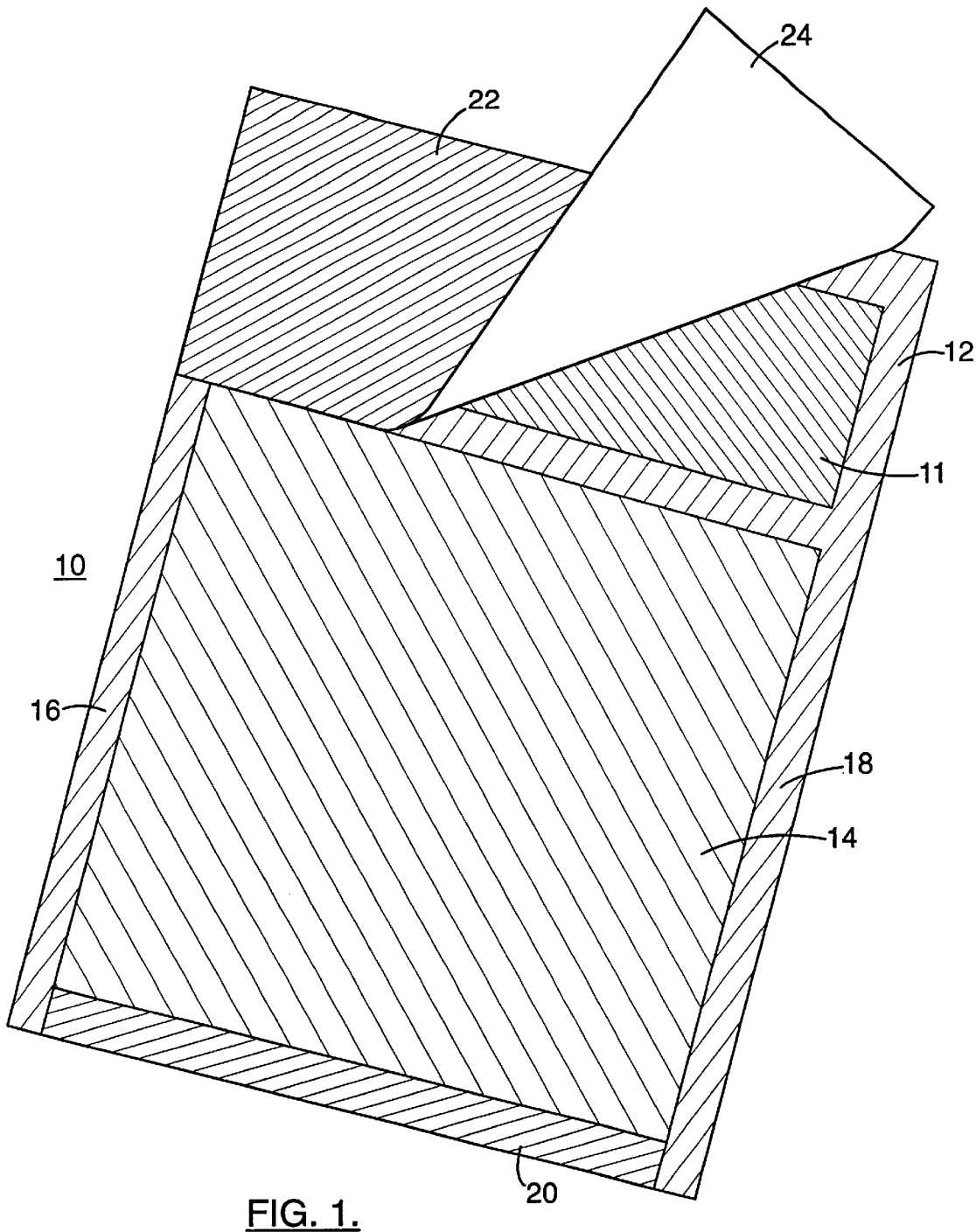
FIG. 1 is a plan view of a non-reinforced package.

FIG. 1 shows a plan view of a non-reinforced sterilizable bag with the header material pealed back to expose the access opening. Sterilizable bag 10 comprises bottom sheet 12 and top sheet 14. Longitudinal side edges 16 and 18 are heat sealed together. Bottom edge 20 is left open or unsealed so that package contents may be inserted therethrough. Header 22 is made from a porous material, preferably medical grade Tyvek®, and is sized according to the width of sheets 12, 14, and the difference in length between sheets 12, 14. The underside 24 of the header 22 is preferably coated with a preferably peelable heat seal coating. The coating is selected to give the desired peelability from the sheets 12 and 14. The medical grade Tyvek® header 22 is heat sealed to sheets 12 and 14 to cover access opening 11.

FIG. 2 shows a close-up cross-sectional view of the heat seal formed by the heat seal at the top edge of the package 10; and the seal formed between the header 22 and the lower sheet 12.

FIG. 3 is an enlarged view of the seal occurring at the header of the present invention. In this figure, tape 30 is adhered to the top edge of the header 22 and is heat sealed to the bottom sheet 12. The tape 30 comprises an adhesive side 32 facing the header 22 and a polymeric backing side 33 facing the sheet 12.

FIG. 4 is a close-up cross-sectional view of the side heat seals formed between sheets 12 and 14.

Figure 5:
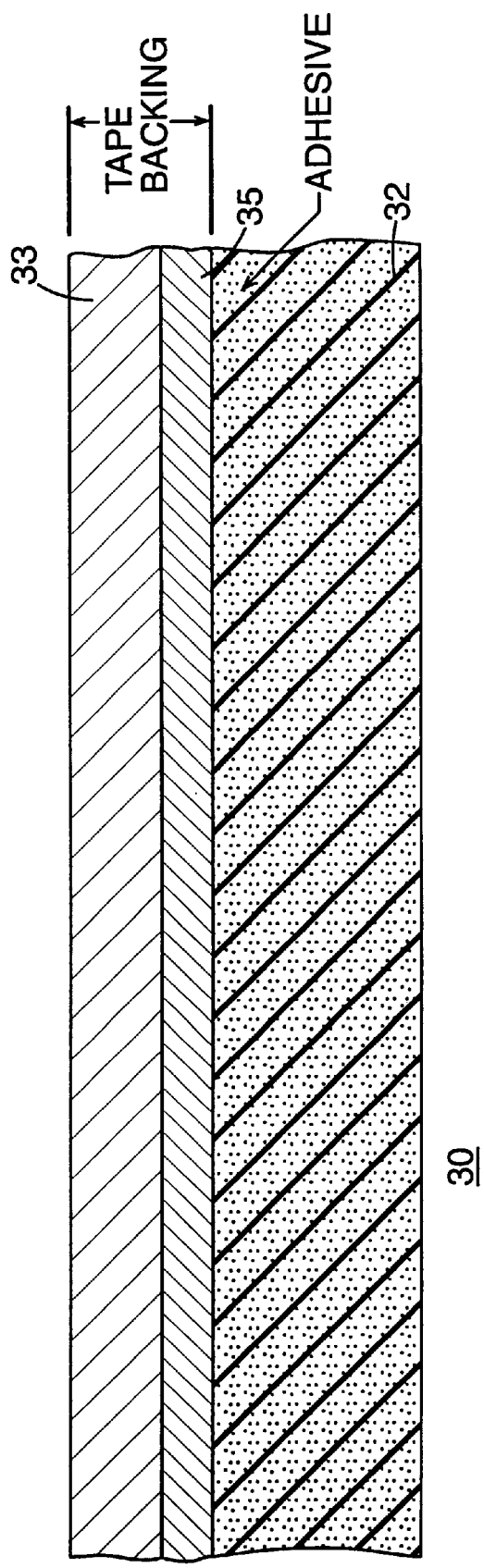
FIG. 5 is a schematic plan view of the adhesive tape used in the present invention.

FIG. 5 shows a cross-sectional view of the tape 30. The tape 30 comprises two or more layers. In one preferred embodiment, tape 30 comprises three layers: (1) preferably a polyethylene layer 33 onto which is coated (2) a polyester layer 35 followed by (3) an adhesive layer 32 coated onto the polyester layer 35. Tapes may have a multiplicity of layers but at least have an adhesive layer and a backing layer.

FIG. 6 shows a schematic view of the process of manufacturing the present invention. FIG. 7 is an overhead plan view of the process line done in schematic form. According to FIGS. 6 and 7, roll 40 releases a header material 42, preferably coated medical grade Tyvek®. The header material 42 feeds past guide roll G 44 and is contacted by tape 41 from roll T 43. The header material with tape 45 then meets the film 46 from roll B 48. The first heat seal 50 is then made thereby joining the header material with tape 45 to the film 46 with a peelable seal. The next film 52 feeds from roll C 54 and has a width approximately equal to the width of header 45 plus film 46 and is then heat sealed 58 at one edge shown in the drawing as the top edge 60. A third heat seal 62 forms the individual bags 64. The top edge 60 is trimmed to provide uniformity at the edge. The transverse or side seals 66, 68 are cut at their approximate center making individual bags that are then stacked 70. In the preferred process as shown, a one-up or two-up process may be carried out. In a two-up process there is no trim, but instead mirror image bags are separated and then cut as would be readily understood by one skilled in the field of bag manufacture.

In the new invention as shown in FIGS. 6 and 7, an adhesive coated film is added to the peelable header at its top edge. The adhesive allows the narrow film to adhere and follow the header, eventually becoming part of the top header heat seal and thus increasing the strength at that top seal. The present invention incorporates many advantages and is a breakthrough in the art of sterile container manufacturing.

The tape and adhesive can be selected to achieve desired results. In certain applications it may be desirable for the header to remain affixed such that the header is not completely separated from the sterile package. For example, in a medical application, such as in an operating room or other medical setting, it may be desirable to keep the total number of separate bag pieces and instruments to a minimum by keeping the header from completely separating from the bag. In this way, one less separate piece is created. The adhesive can be classified as a pressure sensitive, water activated, catalytic cured, uv cured, electron beam cured or moisture cured adhesive.

In other applications, it may be desirable to have the header released completely and easily from the package through the use of a particular adhesive designed to release easily. This also can be accomplished according to the present invention. Regardless of whether an easily releasable adhesive is or is not present, the heat seal between the back of the adhesive tape and the polymeric (eg. polyethylene) sheets used to form the container will remain equally strong, and will be stronger than known bags with respect to the header-to-bag heat seal. In many instances; the tape backing-to-polymeric sheet seal will be at least as strong (less penetrable) as the polymeric sheet-to-polymeric sheet side seals.

It is also understood that the backing of the tape supporting the adhesive layer may be made from polymeric materials including plastics, specifically metallocene catalyzed resins, polyesters, polyethylenes, other bondable backing materials or blends, coextrusions, laminations or combinations made therefrom.

The present invention may be used with any type of container, but is particularly useful for sterilizable bags, pouches, trays, etc. The preferred containers of the present invention can be made out of any material that can be sealed via heat, ultra sonic energy, gluing, etc., and is preferably made from polymeric materials including thermoplastic materials such as polyolefins, ionomers, polyamides, polyurethanes, polyesters, metal foils or mixtures thereof including coextruded films comprising mixed layers of the above, with polyethylene being particularly preferred.

The header of the present invention may be made from any porous medical grade paper, polymeric film or breathable polymeric material, such as spunbonded polyolefin, with heat sealed coated medical grade Tyvek® being particularly preferred.

The foregoing is but one example of the variations which are envisioned as being within the spirit of the invention. For example, it is contemplated that one or more or even all of the edges of a header have the adhesive tape applied depending upon the package requirements. Further, it is also contemplated that the adhesive or the plastic sheet material could be treated or pigmented to yield a particular effect upon heat sealing so that a user would perceive a properly sealed edge. Pigmenting compounds such as titanium dioxide-containing compounds are particularly preferred.

Many other modifications and variations of the present invention are possible to the skilled practitioner in the field in light of the teachings herein. It is therefore understood that within the scope of the claims, the present invention can be practiced other than as herein specifically described.

What is claimed:

1. A method of making a package comprising the steps of:

providing a first layer of polymeric material having a top, bottom and side edges, and having a first length;

providing a header having a top edge lengthwise;

providing a film, said film having a heat sealable polymeric backing side and an adhesive layer, said adhesive layer positioned adjacent the header, said film having a width substantially less than the width of the header;

adhering the film to the header;

providing a second layer of polymeric material having top, bottom, and side edges, said second layer having a second length approximately equal to the combined length of the first polymeric sheet and the header;

registering the second layer of polymeric material and the header;

heat sealing the header to the second layer of polymeric sheet material at the top edge of said second layer;

registering the second layer of polymeric material to the first layer;

registering the top edge of the header to the first layer at the top edge of the first layer;

sealing the first and second layers at the respective side edge; and cutting the heat sealed first and second layers at the side edge to sever a partially sealed container.

2. The method according to claim 1, wherein the first and second polymeric sheet materials comprise materials selected from the group consisting of polyolefins, ionomers, polyamides, polyurethanes, polyesters metal foils and combinations thereof.

3. The method according to claim 1, wherein the header is made from a material selected from the group consisting of medical grade paper, spun-bonded polyolefin and polymeric film.

* * * * *